(12) United States Patent
Alwattari et al.

(10) Patent No.: US 6,503,495 B1
(45) Date of Patent: Jan. 7, 2003

(54) COSMETIC COMPOSITIONS HAVING IMPROVED WEAR AND BEAUTY

(75) Inventors: Ali Abdelaziz Alwattari, Cincinnati, OH (US); Edward Martin Bartholomey, Baltimore, MD (US); Edward Dewey Smith, III, Mason, OH (US); David Edmund Tarantino, Sparks, MD (US); David William Walling, Parkton, MD (US)

(73) Assignee: The Procter & Gamble Company, Cincinnati, OH (US)

( * ) Notice: Subject to any disclaimer, the term of this patent is extended or adjusted under 35 U.S.C. 154(b) by 891 days.

(21) Appl. No.: 08/951,285

(22) Filed: Oct. 16, 1997

Related U.S. Application Data

(63) Continuation of application No. 08/740,578, filed on Oct. 31, 1996.

(51) Int. Cl.$^7$ .............................. A61K 7/06; A61K 6/00; A61K 7/00
(52) U.S. Cl. ..................... 424/70.7; 424/401; 514/938
(58) Field of Search .................... 424/401, 63, 707, 424/70.1, 70.7; 514/938

(56) References Cited

U.S. PATENT DOCUMENTS

| | | | |
|---|---|---|---|
| 3,639,572 A | 2/1972 | Heinrich et al. | 424/63 |
| 4,423,031 A | 12/1983 | Murui et al. | 424/63 |
| 4,917,883 A | 4/1990 | Strobridge | 424/59 |
| 5,356,627 A | 10/1994 | Da Cunha et al. | 424/401 |
| 5,389,363 A | 2/1995 | Snyder et al. | 424/70.7 |
| 5,420,218 A * | 5/1995 | Toribuchi | 526/214 |
| 5,480,632 A * | 1/1996 | Orr et al. | 424/63 |
| 5,620,693 A | 4/1997 | Piot et al. | 424/401 |

FOREIGN PATENT DOCUMENTS

| | | | |
|---|---|---|---|
| EP | 0 530 084 A1 | 3/1993 | A61K/7/48 |
| EP | 0 568 035 A2 | 3/1993 | A61K/7/02 |
| EP | 0 557 196 B1 | 8/1993 | A61K/7/00 |
| GB | 2 021 411 A | 12/1979 | A61K/7/00 |
| GB | 2 238 242 A | 11/1990 | A61K/7/032 |
| JP | 07-267817 | 10/1995 | A61K/7/02 |
| JP | 07-267828 | 10/1995 | A61K/7/032 |
| WO | WO 91/12793 | 9/1991 | A61K/7/032 |
| WO | WO 92/19215 | 11/1992 | A61K/7/032 |
| WO | WO 93/16684 | 9/1993 | A61K/7/48 |
| WO | WO 96/33690 | 10/1996 | A61K/7/032 |
| WO | WO 96/36308 | 11/1996 | A61K/7/00 |

OTHER PUBLICATIONS

Abstract: J5 5130–906, published Oct. 11, 1980 Derwent Publications Ltd.
NL Industries, Inc., "Controlling Cosmetic Pheology", p. 6, 1985.
Othmer, "Latex Technology", *Encyclopedia of Chem. Tech.* vol. 14, 3rd Ed., 1981.
Lan et al., "Polymer–Clay Nanocomposite Materials", *CMS Courier*, vol. 1, Issue 8, pp. –3, 1994.
Grim, "Organically Modified Clay Mastergels—A New Approach to Cosmetic Formulating", *Mineralogy*, 2nd Ed., McGraw–Hill, N.Y., p. 31–35, 1968.
Wilkinson et al., *Harry's Cosmeticology*, 7th Ed., p. 738, 1982.
Schick et al., Surfactant Science Series, vol. 2, *Solvent Properties Surfactant Solutions*, p. 607. 1966.
C.T.F.A. Cosmetic Ingredient Handbook, pp. 587–592, 1992. 1997.
Remington's Pharmaceutical Sciences, 15th Ed., pp. 335–337, 1975.
McCutcheion's, vol. 1, *Emulsifiers & Detergents*, N. Amer. Ed., pp. 236–239, 1994.
Abstract: JP 08 084921 A, published Apr. 2, 1996 Patent Abstracts of Japan.
Abstract: JP 08 217619 A, published Aug. 27, 1996 Patent Abstracts of Japan.
Derwent Abstract NO. 96–224461/23 (JP08084921–A), published Apr. 2, 1996.
Derwent Abstract No. 96–439418/44 (JP08217619–A), published Aug. 27, 1996.

\* cited by examiner

*Primary Examiner*—Russell Travers
*Assistant Examiner*—Lauren Q. Wells
(74) *Attorney, Agent, or Firm*—Dara M. Kendall; George W. Allen; Tara M. Rosnell

(57) ABSTRACT

The present invention relates to oil-in-water mascara compositions comprising water-insoluble polymeric materials in the form of an aqueous emulsion, water-soluble, film-forming polymers and organophilic clays. Said compositions exhibit improved wear and are removable with soap and water.

26 Claims, No Drawings

COSMETIC COMPOSITIONS HAVING IMPROVED WEAR AND BEAUTY

This is a continuation of application Ser. No. 08/740,578, filed Oct. 31, 1996.

TECHNICAL FIELD

The present invention relates to cosmetic compositions, particularly eye make-up compositions, most particularly mascaras, comprising water-insoluble polymeric material in the form of an aqueous emulsion and water-soluble, film-forming polymers. In addition, the compositions herein utilize organophilic clays wherein the clays physically complex with the polymers. This serves to reinforce the film applied to the lashes such that smudging & smearing of the mascara is prevented.

BACKGROUND OF THE DISCLOSURE

Eye make-up compositions, including mascara, are significant products in the cosmetics market. Mascara enhances the beauty of the wearer by coating the eye lashes, or in some instances eyebrows, with color.

In spite of their beauty enhancing characteristics, conventional eye make-up preparations have been criticized for their failure to produce the desired effects during long periods of wear. Problems such as staining and smearing, commonly referred to as smudging, and flaking of the mascara from the eyelashes are well known. Even where longevity has been improved, such compositions also are known to be difficult to completely remove from the delicate eye area. An eye makeup composition conceptually having significantly superior wear life, yet, easy removability with soap and water would be very desirable. Furthermore, the mascara should provide beauty benefits, particularly in terms of application benefits to the user.

Eye makeup compositions comprising polymeric emulsions in order to eliminate smudging are well known in the art and typically include water-insoluble polymers, also referred to as latexes. Such compositions including eye shadows as disclosed in U.S. Pat. No. 3,639,572, Henrich, issued Feb. 1, 1972; and mascaras as disclosed in U.S. Pat. No. 4,423,031, Murui et al., issued Dec. 27, 1983; and European Patent Application (EPA) 0568035, published Nov. 3, 1993. These compositions include plasticizers or solvents to assist in forming films using said latexes. These compositions are known to contain thickeners to adjust the viscosity of the composition. Said thickeners include water-soluble and water-swellable polymers, typically known for such use in the cosmetic art.

A different embodiment of the above concept is disclosed in Patent Cooperation Treaty application WO 94/17775, published Aug. 18, 1994. The invention disclosed therein includes mascara compositions comprising waterbased silicone elastomeric latex emulsions as opposed to "waterbased" acrylic polymers. Longer wear and durability is attributed to the use of the elastomeric latex as it is more compatible with the rest of the compositional matrix than the acrylic polymers.

Other compositions known in the art that avoid combining plasticizers and insoluble-polymers are exemplified in EPO 0530084, published Mar. 3, 1993. This application discloses compositions comprising a internal phase and a external phase, wherein the external phase contains at least one water-soluble polymer and the internal phase contains at least 50% wax. Said composition may contain other materials routinely used in cosmetic compositions including water-insoluble polymers.

L'Oreals patent application, WO 91/12793, published May 4, 1994, discloses water-resistant composition for eyelashes containing at least one wax, at least one "consistency" agent, at least one volatile organic solvent and 1–35% (by weight of the composition) of an aqueous solution of at least one water-soluble, film-forming polymer. The level of water-soluble, film-forming polymers is between 0.1% and 55%, and does not contain any emulsifying agents. The processing instructions direct one to disperse the aqueous phase into the oil phase thereby making the composition a water-in-oil emulsion. Furthermore, the "consistency agent" (referred to in the specification as a "stability agent") is selected from the group of organically treated argyles.

Organophilic clays are known for use with organic solvent and oil based systems. The benefits derived from the use of organophilic clays in these systems is three-fold. Organophilic clays provide viscosity, flow control and stability to these solvent-based and oil-based systems. This is similar to the way hydrophilic clay thickeners are used water-based products. For example, organoclay, reaction products of an organic quaternary amine with either hectorite or bentonite clay, are capable of swelling and gelling above mentioned organic-based systems to gel various hydrocarbon and natural oils, solvents and synthetic liquids; see "Controlling Cosmetic Rheology," NL Industries (1985), p6.

Included among organic solvent-based and oil solvent-based systems are those which are anhydrous or contain water as the dispersed phase as in water-in-oil emulsion systems. Regardless of which of the organic or oil based system are employed, it is understood that the organophilic clays are dispersed in the lipophilic phase to thicken the viscosity of the oils and the vehicle overall. In this manner, they may also be combined with oil-soluble polymeric or resin materials.

Until now, however, nowhere has it been disclosed that non-organic solvent or oil based systems such as oil-in-water emulsions can benefit from the use of organophilic clays. By experimentation and ingenuity, it has been surprisingly found incorporating organophilic clays into oil-in-water cosmetic compositions as disclosed herein provides additional wear and beauty benefits not realized in the art.

SUMMARY OF THE INVENTION

The present invention is for mascara compositions, removable with soap and water, that provide surprising beauty and wear benefits as compared to compositions known in the art. These compositions comprise from about 3% to about 60% water-insoluble polymeric material, from about 2% to about 50% water-soluble, film-forming polymers, and from about 0.05% to about 20.0% organophilic clays.

Compositions of the present invention can be fabricated in a multitude of forms, such as creams, pastes and solids. All percentages are by weight of the cosmetic composition unless otherwise indicated. All solutions are on a weight/weight concentration unless otherwise indicated.

DETAILED DESCRIPTION OF THE INVENTION

A. Water-insoluble Polymeric Materials

The mascara composition of the present invention comprises water-insoluble polymeric materials in an aqueous emulsion. Said water-insoluble polymeric materials, disclosed in the art as latexes, are aqueous emulsions or dispersions of polymeric materials comprising polymers formed from monomers, said monomer derivatives, mixtures of said monomers, mixtures of said monomer derivatives, natural polymers and mixtures thereof. Said polymeric material also include chemically modified versions of the above polymers. These water-insoluble polymeric materials of the present invention comprise from about 3% to about 60%; preferably from about 4% to about 40% and most preferably from about 5% to about 30% by weight of the composition.

Water-insoluble polymeric material of the present invention comprise monomers selected from the group consisting of aromatic vinyls, dienes, vinyl cyanides, vinyl halides, vinylidene halides, vinyl esters, olefins and their isomers, vinyl pyrrolidone, unsaturated carboxylic acids, alkyl esters of unsaturated carboxylic acids, hydroxy derivatives of alkyl esters of unsaturated carboxylic acids, amides of unsaturated carboxylic acids, amine derivatives of unsaturated carboxylic acids, glycidyl derivatives of alkyl esters of unsaturated carboxylic acids, olefinic diamines and isomers, aromatic diamines, terephthaloyl halides, olefinic polyols and mixtures thereof. Preferred monomers are selected from the group consisting of aromatic vinyls, dienes, vinyl esters, olefins and their isomers, unsaturated carboxylic acids, alkyl esters of unsaturated carboxylic acids, hydroxy derivatives of alkyl esters of unsaturated carboxylic acids, amides of unsaturated carboxylic acids and mixtures thereof. Most preferred monomers are selected from the group consisting of aromatic vinyls, dienes, vinyl esters, alkyl esters of unsaturated carboxylic acids, hydroxy derivatives of alkyl esters of unsaturated carboxylic acids and mixtures thereof. The polymerization process for making said polymeric material of the present invention is well known in the art. Such processes are disclosed in Kirk Othmer, *Encyclopedia of Chemical Technology*, Volume 14, "Latex Technology" 3rd Ed. 1981; incorporated herein by reference.

Specific polymeric material useful in the present invention include, but, are not necessarily limited to the Syntran Series (of latexes) from Interpolymer Corporation, for example Syntran 5170, Syntran EX33-1, Syntran EX30-1, and Syntran 5130 (acrylates copolymers formulated with added ammonia, propylene glycol, preservative and surfactant) and Syntran 5002 (styrene/acrylates/methacrylate copolymer formulated with added ammonia, propylene glycol, preservative and surfactant); the Primal Series (acrylic latexes) from Rohm & Hass; Appretan V (styrene/acrylic ester copolymer latexes) from Hoechst; Vinac (polyvinylacetate latex) from Air Products; UCAR latex resin 130 (polyvinylacetate latex) from Union Carbide; Rhodopas A Series (polyvinylacetate latexes) from Rhone Poulenc; Appretan MB, EM, TV (vinyl acetate/ethylene copolymer latexes) from Hoechst; 200 Series (styrene/butadiene copolymer latexes) from Dow Chemical; Rhodopas SB Series (styrene/butadiene copolymer latexes) from Rhone Poulenc; Witcobond (polyurethane latexes) from Witco; Hycar Series (butadiene/acrylonitrile copolymer latexes) from Goodrich; Chemigum Series (butadiene/acrylonitrile copolymer latexes) from Goodyear; and Neo Cryl (styrene/acrylates/acrylonitrile copolymer latex) from ICI Resins.

B. Water-soluble, Film Forming Polymers

In addition to the water-insoluble polymeric material disclosed above, the mascara composition of the present invention comprises water-soluble, film forming polymers. Water-soluble, film-forming polymers are defined herein to mean polymers which are soluble in water, water-cosolvent mixtures, such as ethanol/water, pH adjusted water, and/or tempered solutions of the above to facilitate solubilization of the polymers. Water-soluble, film forming polymers comprise from about 0.1% to about 50%, preferably from about 1% to about 30%, and most preferably from about 1.5% to about 10% of the composition.

The film forming, water-soluble polymers comprise polymers formed from monomers, said monomer derivatives, mixtures of said monomers, mixtures of said monomer derivatives, natural polymers and mixtures thereof. The water-soluble, film forming polymers disclosed herein also include chemically modified versions of the above disclosed polymers. Said monomers are selected from the group consisting of olefin oxides, vinyl pyrrolidone, vinyl esters, vinyl alcohols, vinyl cyanides, oxazoline, carboxylic acids and esters and mixtures thereof. Preferred vinyl pyrrolidone polymers are selected from the group consisting of polyvinylpyrrolidone, vinyl acetate/vinyl pyrrolidone copolymer and mixtures thereof. Preferred polyvinyl esters are selected form the group consisting of vinyl acetate/crotonic acid copolymer, vinyl acetate/crotonic acid/vinyl neodecanoate copolymer and mixtures thereof Preferred vinyl alcohol polymers are selected from the group consisting of vinyl alcohol/vinyl acetate, vinyl alcohol/poly (alkyleneoxy)acrylate, vinyl alcohol/vinyl acetate/poly-(alkyleneoxy)acrylate and mixtures thereof. Preferred olefin oxides are selected from the group consisting of polyethylene oxide, polypropylene oxide and mixtures thereof. Preferred polycarboxylic acids and their esters are selected from the group consisting of acrylates, acrylates/otylacrylamide copolymers and mixtures thereof. The preferred oxazoline is polyoxazoline.

Water-soluble, film forming polymers of the present invention comprise natural polymers selected from the group consisting of cellulose derivatives, algin and its derivatives, starch and its derivatives, guar and its derivatives, shellac polymers, and mixtures thereof. Preferred cellulose derivatives are selected from the group consisting of hydroxyethylcellulose, hydroxypropylcellulose, hydroxypropyl methylcellulose, ethylhydroxyethyl cellulose and mixtures thereof.

Specific water-soluble, film-forming polymers used in the present invention include, but are not necessarily limited to Polyox WSR (polyethyleneoxide polymers) from Union Carbide; Natrosol 250 (hydroxyethylcellulose) from Aqualon; Cellosize (hydroxyethylcellulose) from Union Carbide; Airvol (polyvinylalcohol copolymer) from Air Products and Chemicals, preferably all commercially available grades like Airvol 103, Airvol 325, Airvol 540, Airvol 523S; Vinex from Air Products and Chemicals, preferably all commercially available grades such as Vinex 1003, Vinex 2034, Vinex 2144, Vinex 2019; PEOX (polyethyloxazoline) from Polymer Chemistry Innovations; PVP K Series (polyvinylpyrrolidone) from International Specialty Products; Luviskol K Series (polyvinylpyrrolidone) from BASF; PVP/VA (vinyl acetate/vinyl pyrrolidone copolymer) from International Specialty Products, preferably grades W-735 and S630; and Gantrez (copolymers of methyl vinyl ether/maleic anhydride) from International Specialty Products; Carboset Series (acrylate copolymer) from BF Goodrich; Resyn Series (vinyl acetate/crotonate copolymers) from National Starch and Chemical Corporation; Versatyl and Dermacryl Series (acrylate/octylacrylamide copolymers) from National Starch and Chemical Corporation.

C. Organophilic Clays

As previously disclosed, orgaophilic clays are know for use in organic solvent-based and oil-based systems, including anhydrous and water-in-oil mascara compositions.

While such a system is known for industrial use, it has not been previously applied to the cosmetic arts; see Tie Lan and Dr. T. J. Pinnavaia (Dept. of Chemistry), CMS Courier, Vol I Issue 8, July 1994; "Polymer-Clay Nanocomposite Materials", pp.2–3 disclosing the addition of organophilic clays to nylon-6, improve the tensile strength, modulus, rheology and thermal capacity of plastics used in automobile production. We have found that the application of organophilic clays used in sufficient concentrations within an aqueous-based or oil-in-water emulsions results in providing mascara compositions with surprising results including the formation of a physical complex with the water-insoluble, film-forming polymers in the present invention. This complexing of the clays and film-forming polymers yields a composite film that is reinforced by the organophilic clay and thereby preventing smudging or smearing of the product, especially in the case of mascaras. Additionally, the hydrophobic properties of organophilic clays are transferred to the aqueous-based emulsion, thereby imparting a degree of water-resistance to the product. Therefore, a new set of benefits is realized, different from conventional teachings in the cosmetic industry. And these benefits directly impact the overall stability of the cosmetic film on the substrate resulting in long-wear for the consumer.

The organophilic clays are used at levels from about 0.05% to about 20.0%, preferably 1% to about 10% and most preferably from about 2% to about 5% of the compositions of the present invention. Whether the clay is commercially available or not is not a limitation of the present invention. However, the commercially clays are logically preferred.

Clays are generally considered amorphous and crystalline. Among the amorphous clays are those that belong to the allophane group. Crystalline types of clays include two-layer type clays, three layer-type clays, regular mixed-layer type clays and chain structure type clays; see Grim, R. E. *Mineralogy*, Second Edition, McGraw-Hill, N.Y., 1968.

Two-layer type clays include those that are equi-dimensional and elongate. Equi-dimensional clays include the kaolinite group of clays. The elongate clays include the halloysite group of clays. Three-layer type clays include expanding lattice clays including equi-dimensional and elongate clays as well as non-expanding lattice clays. Expanding lattice, equi-dimensional clays include smectite and vermiculite groups of clays. The smectite group of clays consists of montmorillonite, bentonite and sauconite. Expanding lattice, elongate clays include the smectite group of clays consisting of nontronite hectorite and saponite. The non-expanding lattice clays include illite. The regular mixed-layer type clays include the chlorite group of clays. The chain structure types of clays include attapulgite and sepiolite types of clay.

Organophilic clays are formed by modifying the above identified clays with compounds selected from the group consisting of quaternary amines, tertiary amines, amine acetates, imidazolines, amine soaps, fatty sulfates, alkyl aryl sulfonates, amine oxides, ethoxylated alkyl phenols and mixtures thereof. These materials are combined with the above clays under ion-exchange conditions renders the clays organophilic.

Among the preferred organically-modified clays for used as the organophilic clays of the present invention are those selected from the group of montmorillonite, bentonite, hectorite, attapulgite, sepiolite and mixtures thereof. Among these organophilic clays for use in the present invention are the following commercially available ones including:

Bentone 34 (Rheox Corp.)—Quaternium-18 Bentonite;
Tixogel VP (United Catalysts)—Quaternium-18 Bentonite;
Bentone 38 (Rheox Corp.)—Quaternium-18 Hectorite;
Bentone SD-3 (Rheox Corp.)—Dihydrogenated Tallow Benzylmonium Hectorite;
Bentone 27 (Rheox Corp.)—Stearalkonium Hectorite;
Tixogel LG (United Catalysts)—Stearalkonium Bentonite;
Claytone 34 (Southern Clay) Quaternium-18 Bentonite;
Claytone 40 (Southern Clay) Quaternium-18 Bentonite;
Claytone AF (Southern Clay) Stearalkonium Bentonite;
Claytone APA (Southern Clay) Stearalkonium Bentonite;
Claytone GR (Southern Clay) Quaternium-18/Benzalkonium Bentonite;
Claytone HT (Southern Clay) Quaternium-18/Benzalkonium Bentonite;
Claytone PS (Southern Clay) Quaternium-18/Benzalkonium Bentonite;
Claytone XL (Southern Clay) Quaternium-18 Bentonite; and
Vistrol 1265 (Cimbar)—Organophilic Attapulgite.

The above organophilic clays can also be purchased as pre-dispersed organophilic clay in either an oil or an organic solvent. The materials are in the form of a heavy paste that can be readily dispersed into the formulation. Such materials include Mastergels by Rheox, United Catalysts, and Southern Clay.

The compositions of this invention contain an effective amount of "activator" for the organically modified hectorite and bentonite clays. Many such activators are known in the art, including for example, propylene carbonate, ethanol, and mixtures thereof. The preferred activator for use is propylene carbonate. Preferably, the ratio of clay to activator is about 3:1.

Optional Ingredients

Optional ingredients useful in the present invention are selected based on either the various forms or attributes the composition is to have. The most preferred embodiments of the present invention are oil-in-water emulsions. Some of the most common optional ingredients include oils and fats, emulsifiers, waxes, pigments and mixtures thereof.

A. Oils and Fats

Mascara compositions of the present invention include oil-in-water emulsion compositions. These compositions require a lipophilic material which forms the internal phase of the composition. Said lipophilic materials typically comprise oils and fats generally known for use in the cosmetic arts.

Oils typically used in cosmetics include those selected from the group consisting of polar oils, non-polar oils, volatile oils, non-volatile oils and mixtures thereof. These oils may be saturated or unsaturated, straight or branched chained, aliphatic or aromatic hydrocarbons.

Preferred oils include non-polar volatile hydrocarbons including isodecane (such as Permethyl-99A®, available from Presperse Inc.) and the $C_7$–$C_8$ through $C_{12}$–$C_{15}$ iso-paraffins (such as the Isopar® Series available from Exxon Chemicals), as well as cyclomethicone (such as DC Fluids 244, 245, 344, 345).

Fats employed according to the invention are selected from the group consisting of fats derived from animals, vegetables, synthetically derived fats, and mixtures thereof wherein said fats have a melting point from about 55° C. to about 100° C. and a needle penetration, as measured according to the American standard ASTM D5, from about 3 to about 40 at 25° C. Preferably the fats selected for use in the present invention are fatty acid esters which are solids at room temperature and exhibit crystalline structure. Examples of fatty acid esters useful in the present invention include the glyceryl esters of higher fatty acids such as stearic and palmitic such as glyceryl monostearate, glyceryl distearate, glyceryl tristearate, palmitate esters of glycerol, $C_{18-36}$ triglycerides, glyceryl tribehenate and mixtures thereof.

B. Emulsifiers

A necessary components in the oil-in-water-emulsion compositions of the present invention are emulsifiers. In these embodiments of the present invention, emulsifiers are typically used at levels from about 0.1% to about 40%, preferably from about 0.5% to about 30%.

There are many factors which determine whether the water or the oil end up the dispersed or continuous phase. However, the single most important factor is the hydrophilic-lipophilic balance value (herein referred to as HLB) of the emulsifier; Wilkinson and Moore, *Harry's Cosmeticology*, 7th Ed. 1982, p. 738. For example Schick and Fowkes, Surfactant Science Series, Vol. 2, *Solvent Properties of Surfactant Solutions*, p 607. Schick and Fowkes discloses that HLB values of surfactant emulsifiers for making oil-in-water emulsions is from 8–15. Said emulsifiers include those disclosed in the C.T.F.A. Cosmetic Ingredient Handbook, 1992, pp.587–592; and Remington's Pharmaceutical Sciences, 15th Ed. 1975, pp 335–337; both incorporated herein by reference. Said emulsifiers are selected from those known in the art and mixtures thereof including those in McCutcheon's Volume 1, *Emulsifiers & Detergents*, 1994, North American Edition, pp. 236–239; herein incorporated by reference.

C. Waxes

Waxes are defined as lower-melting organic mixtures or compounds of high molecular weight, solid at room temperature and generally similar in composition to fats and oils except that they contain no glycerides. Some are hydrocarbons, others are esters of fatty acids and alcohols. Waxes useful in the present invention are selected from the group consisting of animal waxes, vegetable waxes, mineral waxes, various fractions of natural waxes, synthetic waxes, petroleum waxes, ethylenic polymers, hydrocarbon types such as Fischer-Tropsch waxes, silicone waxes, and mixtures thereof wherein the waxes have a melting point between 55° and 100° C. and a needle penetration, as measured according to the American standard ASTM D5, of 3 to 40 at 25° C. The principle of the measurement of the needle penetration according to the standards ASTM D5 consists in measuring the depth, expressed in tenths of a millimeter, to which a standard needle (weighing 2.5 g and placed in a needle holder weighing 47.5 g, i.e. a total of 50 g) penetrates when placed on the wax for 5 seconds. Waxes are used at levels in order to provide sufficient bulk material that resists drying out after application, providing thickness to the lashes. Levels of wax commonly found in the art are from about 1% to about 40%.

The specific waxes useful in the present invention are selected from the group consisting of beeswax, lanolin wax, shellac wax (animal waxes); carnauba, candelilla, bayberry (vegetable waxes); ozokerite, ceresin, (mineral waxes); paraffin, microcrystalline waxes (petroleum waxes); polyethylene, (ethylenic polymers); polyethylene homopolymers (Fischer-Tropsch waxes); $C_{24-45}$ alkyl methicones (silicone waxes); and mixtures thereof Most preferred are beeswax, lanolin wax, carnauba, candelilla, ozokerite, ceresin, paraffins, microcrystalline waxes, polyethylene, $C_{24-45}$ alkyl methicones, and mixtures thereof.

D. Pigments

The solids component of the mascara compositions of the present invention contain cosmetically acceptable pigments selected from the group consisting of inorganic pigments, organic pigments, and pearlescent pigments. When employed, the pigments are present in proportions depending on the color and the intensity of the color which it is intended to produce. The level of pigments in the solid portion of the mascara composition of present invention is from about 3% to about 30%, preferably from about 5% to about 20%. Pigments are selected from the group consisting of inorganic pigments, organic lake pigments, pearlesent pigments, and mixtures thereof. Said pigments may optionally be surface-treated within the scope of the present invention but are not limited to treatments such as silicones, perfluorinated compounds, lecithin, and amino acids.

Inorganic pigments useful in the present invention include those selected from the group consisting of rutile or anatase titanium dioxide, coded in the Color Index under the reference CI 77,891; black, yellow, red and brown iron oxides, coded under references CI 77,499, 77, 492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

The organic pigments and lakes useful in the present invention include those selected from the group consisting of D&C Red No. 19 (CI 45,170), D&C Red No. 9 (CI 15,585), D&C Red NO. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430) and the dye or lakes based on Cochineal Carmine (CI 75,570) and mixtures thereof.

The pearlescent pigments useful in the present invention include those selected from the group consisting of the white pearlescent pigments such as mica coated with titanium oxide, bismuth oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

E. Miscellaneous

In the present invention numerous optional ingredients may be added to provide additional benefits other than that attributed to the invention as defined above. For example, it is preferred that the mascara composition of the present invention contain a preservative system to inhibit microbiological growth and maintain the integrity of the product. In the present invention, the preservative system does not have a detrimental effect on the composition.

Any optional ingredients known to those skilled in the art may also be used in the invention. Examples of optional ingredients are cosmetic fillers including, but not limited to, mica, talc, nylon, polyethylene, silica, polymethacrylate, kaolin, teflon; cosmetic preservatives including, but not limited to, methylparaben, propylparaben, butylparaben, ethylparaben, potassium sorbate, trisodium EDTA, phenoxyethanol, ethyl alcohol, diazolidinyl urea, benzyl alcohol, imidazolidinyl urea, quaternium-15. Also, additives such as tall oil glycerides are easily incorporated into emulsion forms of the mascara.

EXAMPLES

Example #1

| Ingredient | W/W % |
|---|---|
| Deionized Water | 49.96 |
| Synthetic Wax | 7.00 |
| Glycerol Monostearate | 3.00 |
| Carnauba Wax | 2.00 |
| Black Iron Oxide | 7.25 |
| Quaternium-18 Hectorite[1] | 4.00 |
| Propylene Carbonate | 1.33 |
| Stearic Acid | 2.75 |
| Oleic Acid | 0.75 |
| Triethanolamine | 1.75 |
| Trisodium EDTA | 0.10 |
| Polyvinyl Alcohol | 3.00 |
| Propylene Glycol | 2.00 |
| Simethicone[2] | 0.20 |
| Ammonium Acrylates Copolymer[3] | 12.20 |
| Ethyl Alcohol[4] | 1.00 |
| Benzyl Alcohol | 0.65 |
| Phenoxyethanol | 0.28 |
| Propylparaben | 0.10 |
| Methylparaben | 0.20 |
| Ethylparaben | 0.20 |
| Panthenol[5] | 0.28 |

[1]available as Bentone 38 from Rheox.
[2]available as Antifoam from Dow Corning.
[3]available as Syntran EX33-1 (41% Stock Solution) from Interpolymer Corporation.
[4]available as SD Alcohol 40-B from Warner Graham Company.
[5]available as dl-Panthenol from Roche.

Example #2

| Ingredient | W/W % |
|---|---|
| Deionized Water | 40.18 |
| Synthetic Wax | 1.50 |
| Glycerol Monostearate | 7.25 |
| Carnauba Wax | 2.00 |
| Black Iron Oxide | 7.25 |
| Quaternium-18 Hectorite[1] | 3.75 |
| Propylene Carbonate | 1.25 |
| Stearic Acid | 2.75 |
| Oleic Acid | 1.00 |
| Triethanolamine | 1.75 |
| Xanthan Gum | 0.10 |
| Trisodium EDTA | 0.10 |
| Polyvinyl Alcohol | 1.50 |
| Acrylates Copolymer[2] | 5.17 |
| Propylene Glycol | 2.00 |
| Simethicone[3] | 0.20 |
| Ammonium Acrylates Copolymer | 18.29 |
| Lecithin | 1.25 |
| Ethyl Alcohol[5] | 1.00 |
| Benzyl Alcohol | 0.65 |
| Phenoxyethanol | 0.28 |
| Propylparaben | 0.10 |
| Methylparaben | 0.20 |
| Ethylparaben | 0.20 |
| Panthenol[6] | 0.28 |

[1]available as Bentone 38 from Rheox.
[2]available as Carboset xpd-1616 (29% Stock Soln) from B F Goodrich.
[3]available as Antifoam from Dow Corning.
[4]available as Syntran EX33-1 (41% Stock Solution) from Interpolymer Corporation.
[5]available as SD Alcohol 40-B from Warner Graham Company.
[6]available as dl-Panthenol from Roche.

Example #3

| Ingredient | W/W % |
|---|---|
| Deionized Water | 41.95 |
| Synthetic Wax | 3.00 |
| Glycerol Monostearate | 6.00 |
| Carnauba Wax | 4.50 |
| Black Iron Oxide | 7.25 |
| Quaternium-18 Hectorite[1] | 2.25 |
| Propylene Carbonate | 0.75 |
| Stearic Acid | 2.75 |
| Oleic Acid | 0.75 |
| Triethanolamine | 1.75 |
| Trisodium EDTA | 0.10 |
| Polyvinyl Alcohol | 4.00 |
| Acrylates Copolymer[2] | 1.72 |
| Propylene Glycol | 2.00 |
| Simethicone[3] | 0.20 |
| Ammonium Acrylates Copolymer[4] | 17.07 |
| Lecithin | 1.25 |
| Ethyl Alcohol[5] | 1.00 |
| Benzyl Alcohol | 0.65 |
| Phenoxyethanol | 0.28 |
| Propylparaben | 0.10 |
| Methylparaben | 0.20 |
| Ethylparaben | 0.20 |
| Panthenol[6] | 0.28 |

[1]available as Bentone 38 from Rheox.
[2]available as Carboset xpd 1616 (29% Stock Soln) from B F Goodrich.
[3]available as Antifoam from Dow Corning.
[4]available as Syntran EX33-1 (41% Stock Solution) from Interpolymer Corporation.
[5]available as SD Alcohol 40-B from Warner Graham Company.
[6]available as dl-Panthenol from Roche.

Example #4

| Ingredient | W/W % |
|---|---|
| Deionized Water | 41.15 |
| Synthetic Wax | 4.00 |
| Glycerol Monostearate | 6.00 |
| Carnauba Wax | 3.75 |
| Black Iron Oxide | 9.00 |
| Quaternium-18 Hectorite[1] | 4.00 |
| Propylene Carbonate | 1.33 |
| Stearic Acid | 2.75 |
| Oleic Acid | 1.00 |
| Triethanolamine | 1.75 |
| Trisodium EDTA | 0.10 |
| Propylene Glycol | 1.00 |
| Simethicone[2] | 0.20 |
| Ammonium Acrylates Copolymer[3] | 19.51 |
| Lecithin | 1.75 |
| Ethyl Alcohol[4] | 1.00 |
| Benzyl Alcohol | 0.65 |
| Phenoxyethanol | 0.28 |
| Propylparaben | 0.10 |
| Methylparaben | 0.20 |
| Ethylparaben | 0.20 |
| Panthenol[5] | 0.28 |

[1]available as Bentone 38 from Rheox.
[2]available as Antifoam from Dow Corning.
[3]available as Syntran EX33-1 (41% Stock Solution) from Interpolymer Corporation.
[4]available as SD Alcohol 40-B from Warner Graham Company.
[5]available as dl-Panthenol from Roche.

Example #5

| Ingredient | W/W % |
| --- | --- |
| Deionized Water | 37.43 |
| Synthetic Wax | 3.00 |
| Glycerol Monostearate | 7.00 |
| Carnauba Wax | 1.00 |
| Black Iron Oxide | 7.25 |
| Quaternium-18 Hectorite[1] | 3.75 |
| Propylene Carbonate | 1.25 |
| Stearic Acid | 2.75 |
| Oleic Acid | 0.75 |
| Triethanolamine | 1.75 |
| Xanthan Gum | 0.40 |
| Trisodium EDTA | 0.10 |
| Polyvinyl Alcohol | 1.00 |
| Acrylates Copolymer[2] | 6.90 |
| Propylene Glycol | 2.00 |
| Simethicone[3] | 0.20 |
| Ammonium Acrylates Copolymer[4] | 19.51 |
| Lecithin | 1.25 |
| Ethyl Alcohol[5] | 1.00 |
| Benzyl Alcohol | 0.65 |
| Phenoxyethanol | 0.28 |
| Propylparaben | 0.10 |
| Methylparaben | 0.20 |
| Ethylparaben | 0.20 |
| Panthenol[6] | 0.28 |

[1]available as Bentone 38 from Rheox.
[2]available as Carboset xpd-1616 (29% Stock Soln) from B F Goodrich.
[3]available as Antifoam from Dow Corning.
[4]available as Syntran EX33-1 (41% Stock Solution) from Interpolymer Corporation.
[5]available as SD Alcohol 40-B from Warner Graham Company.
[6]available as dl-Panthenol from Roche.

Example #6

| Ingredient | W/W % |
| --- | --- |
| Deionized Water | 40.42 |
| Synthetic Wax | 3.00 |
| Glycerol Monostearate | 5.00 |
| Carnauba Wax | 1.00 |
| Micronized Black | 6.50 |
| Quaternium-18 Hectorite[1] | 6.00 |
| Propylene Carbonate | 2.00 |
| Stearic Acid | 2.75 |
| Oleic Acid | 1.00 |
| Triethanolamine | 1.75 |
| Xanthan Gum | 0.10 |
| Trisodium EDTA | 0.10 |
| Polyvinyl Alcohol | 1.00 |
| Acrylates Copolymer[2] | 6.90 |
| Propylene Glycol | 1.00 |
| Semithicone[3] | 0.20 |
| Ammonium Acrylates Copolymer[4] | 17.07 |
| Lecithin | 1.50 |
| Ethyl Alcohol[5] | 1.00 |
| Benzyl Alcohol | 0.65 |
| Phenoxyethanol | 0.28 |
| Propylparaben | 0.10 |
| Methylparaben | 0.20 |
| Ethylparaben | 0.20 |
| Panthenol[6] | 0.28 |

[1]available as Bentone 38 from Rheox.
[2]available as Carboset xpd-1616 (29% Stock Soln) from B F Goodrich.
[3]available as Antifoam from Dow Corning.
[4]available as Syntran EX33-1 (41% Stock Solution) from Interpolymer Corporation.
[5]available as SD Alcohol 40-B from Warner Graham Company.
[6]available as dl-Panthenol from Roche.

Example #7

| Ingredient | W/W % |
| --- | --- |
| Deionized Water | 41.22 |
| Synthetic Wax | 5.00 |
| Glycerol Monostearate | 7.50 |
| Carnauba Wax | 2.75 |
| Black Iron Oxide | 7.50 |
| Quaternium-18 Hectorite[1] | 1.00 |
| Propylene Carbonate | 0.33 |
| Stearic Acid | 2.75 |
| Oleic Acid | 1.00 |
| Triethanolamine | 1.75 |
| Xanthan Gum | 0.40 |
| Trisodium EDTA | 0.10 |
| Polyvinyl Alcohol | 4.00 |
| Acrylates Copolymer[2] | 1.72 |
| Propylene Glycol | 2.00 |
| Antifoam | 0.20 |
| Ammonium Acrylates Copolymer[3] | 17.07 |
| Lecithin | 1.00 |
| Ethyl Alcohol[4] | 1.00 |
| Benzyl Alcohol | 0.65 |
| Phenoxyethanol | 0.28 |
| Propylparaben | 0.10 |
| Methylparaben | 0.20 |
| Ethylparaben | 0.20 |
| Panthenol[5] | 0.28 |

[1]available as Bentone 38 from Rheox.
[2]available as Antifoam from Dow Corning.
[3]available as Syntran EX33-1 (41% Stock Solution) from Interpolymer Corporation.
[4]available as SD Alcohol 40-B from Warner Graham Company.
[5]available as dl-Panthenol from Roche.

Example #8

| Ingredient | W/W % |
| --- | --- |
| Deionized Water | 41.18 |
| Synthetic Wax | 1.50 |
| Glycerol Monostearate | 6.50 |
| Carnauba Wax | 2.75 |
| Black Iron Oxide | 7.25 |
| Quaternium-18 Hectorite[1] | 4.00 |
| Propylene Carbonate | 1.33 |
| Stearic Acid | 2.75 |
| Oleic Acid | 1.00 |
| Triethanolamine | 1.75 |
| Trisodium EDTA | 0.10 |
| Polyvinyl Alcohol | 2.50 |
| Acrylates Copolymer[2] | 1.72 |
| Propylene Glycol | 2.00 |
| Semithicone[3] | 0.20 |
| Ammonium Acrylates Copolymer[4] | 19.51 |
| Lecithin | 1.25 |
| Ethyl Alcohol[5] | 1.00 |
| Benzyl Alcohol | 0.65 |
| Phenoxyethanol | 0.28 |
| Propylparaben | 0.10 |
| Methylparaben | 0.20 |
| Ethylparaben | 0.20 |
| Panthenol[6] | 0.28 |

[1]available as Bentone 38 from Rheox.
[2]available as Carboset xpd-1616 (29% Stock Soln) from B F Goodrich.
[3]available as Antifoam from Dow Corning.
[4]available as Syntran EX33-1 (41% Stock Solution) from Interpolymer Corporation.
[5]available as SD Alcohol 40-B from Warner Graham Company.
[6]available as dl-Panthenol from Roche.

Example #9

| Ingredient | W/W % |
| --- | --- |
| Deionized Water | 41.88 |
| Synthetic Wax | 2.00 |
| Glycerol Monostearate | 5.25 |
| Carnauba Wax | 3.00 |
| Black Iron Oxide | 7.25 |
| Quaternium-18 Hectorite[1] | 4.00 |
| Propylene Carbonate | 1.33 |
| Stearic Acid | 2.75 |
| Oleic Acid | 0.80 |
| Triethanolamine | 1.75 |
| Trisodium EDTA | 0.10 |
| Polyvinyl Alcohol | 2.50 |
| Acrylates Copolymer[2] | 1.72 |
| Propylene Glycol | 2.00 |
| Semithicone[3] | 0.20 |
| Ammonium Acrylates Copolymer[4] | 19.51 |
| Lecithin | 1.25 |
| Ethyl Alcohol[5] | 1.00 |
| Benzyl Alcohol | 0.65 |
| Phenoxyethanol | 0.28 |
| Propylparaben | 0.10 |
| Methylparaben | 0.20 |
| Ethylparaben | 0.20 |
| Panthenol[6] | 0.28 |

[1]available as Bentone 38 from Rheox.
[2]available as Carboset xpd-1616 (29% Stock Soln) from B F Goodrich.
[3]available as Antifoam from Dow Corning.
[4]available as Syntran EX33-1 (41% Stock Solution) from Interpolymer Corporation.
[5]available as SD Alcohol 40-B from Warner Graham Company.
[6]available as dl-Panthenol from Roche.

PROCESSING DIRECTIONS

Place the waxes and fats into a vessel equipped with heating and mixing. Heat the waxes and fats to about 90–95° C. with low speed mixing until liquefied and homogeneous. Add oil-dispersible or oil-soluble components such as pigments and organophilic clays and clay activators. Increase the mixing rate to high and mix until the pigments are uniformly dispersed throughout the lipid mixture; about 30–35 minutes. Add emulsifiers to said lipid mixture while continuing to mix.

In a second vessel equipped with mixing and heating, add water followed by the water-soluble, film-forming polymers, and the remainder of the water-dispersible components. The mixture of water and water-soluble film forming polymers can be made up ahead of the processing of the mascara composition. Mix with heating until this aqueous mixture is about 90–95° C. Q.S. for any water loss from said aqueous mixture.

Slowly combine the two mixtures and mix with a high speed dispersator type mixer. Remove heat source and continue mixing this combined mixture until the temperature of said combined mixture is from about 65° C.–70° C. Q.S. said combined mixture for any water loss, add the preservatives and insoluble polymer component and mix until homogeneous. Cool said combined mixture to about 45–47° C. Add any remaining components. Continue cooling and mixing until said combined mixture is about 27–30° C. Transfer said combined mixture to suitable storage containers for subsequent filling of retail size packaging.

We claim:

1. A mascara composition in the form of an oil-in-water emulsion, which composition comprises a water-insoluble polymeric material in an aqueous emulsion, a water-soluble film-forming polymer and an organophilic clay, wherein said clay is incorporated into the oil component of the oil-in-water emulsion.

2. A mascara composition according to claim 1 comprising:
   a. from about 3% to about 60% of said water-insoluble polymeric material in an aqueous emulsion;
   b. from about 0.1% to about 50% of said water-soluble, film-forming polymer; and
   c. from about 0.05% to about 20% of said organophilic clay.

3. A mascara composition according to claim 1 comprising:
   a. from about 5% to about 30% of said water-insoluble polymeric material in an aqueous emulsion;
   b. from about 1.5% to about 10% of said water-soluble, film forming polymer; and
   c. from about 2% to about 5% of said organophilic clay.

4. A mascara composition according to claim 2 wherein:
   a. said water-insoluble polymeric material comprises a polymer formed from monomers selected from the group consisting of aromatic vinyls, dienes, vinyl cyanides, vinyl halides, vinylidene halides, vinyl esters, olefins and their isomers, vinyl pyrrolidone, unsaturated carboxylic acids, alkyl esters of unsaturated carboxylic acids, hydroxy-substituted alkyl esters of unsaturated carboxylic acids, amides of unsaturated carboxylic acids, amines of unsaturated carboxylic acids, glycidyl-substituted alkyl esters of unsaturated carboxylic acids, olefinic diamines and isomers, aromatic diamines, terephthaloyl halides, olefinic polyols, and mixtures thereof;
   b. said water-soluble, film-forming polymer comprises polymer formed from monomers selected from the group consisting of olefin oxides, vinyl pyrrolidone, vinyl esters, vinyl alcohols, vinyl cyanides, oxazolines, carboxylic acids and esters and mixtures thereof; and
   c. said organophilic clay is selected from the group consisting of organically-modified montmorillonite, bentonite, hectorite, attapulgite, sepiolite and mixtures thereof.

5. A mascara composition according to claim 4 wherein said monomers are selected from the group consisting of aromatic vinyls, dienes, vinyl esters, olefins and their isomers, unsaturated carboxylic acids, alkyl esters of unsaturated carboxylic acids, hydroxy derivatives of alkyl esters of unsaturated carboxylic acids, amides of unsaturated carboxylic acids and mixtures thereof.

6. A mascara composition according to claim 5 wherein said monomers are selected from the group consisting of aromatic vinyls, dienes, vinyl esters, alkyl esters of unsaturated carboxylic acids, hydroxy derivatives of alkyl esters of unsaturated carboxylic acids and mixtures thereof.

7. A mascara composition according to claim 4 wherein the vinyl pyrrolidone polymers are selected from the group consisting of polyvinylpyrrolidone, vinyl acetate/vinyl pyrrolidone copolymer and mixtures thereof.

8. A mascara composition according to claim 4 wherein the vinyl esters polymers are selected from the group consisting of vinyl acetate/crotonic acid copolymer, vinyl acetate/crotonic acid/vinyl neodecanoate copolymer and mixtures thereof.

9. A mascara composition according to claim 4 wherein the vinyl alcohol polymers are selected from the group consisting of vinyl alcohol/vinyl acetate, vinyl alcohol/poly(alkyleneoxy)acrylate, vinyl alcohol/vinyl acetate/poly(alkyleneoxy)acrylate and mixtures thereof.

10. A mascara composition according to claim 4 wherein the olefin oxides polymers are selected from the group consisting polyethylene oxide, polypropylene oxide and mixtures thereof.

11. A mascara composition according to claim 4 wherein the carboxylic acid polymers and esters polymers are selected from the group consisting of acrylates, acrylates/octyl-acrylamide copolymers and mixtures thereof.

12. A mascara composition according to claim 4 wherein the oxazilines polymers are polyoxazilines.

13. A mascara composition according to claim 4 wherein the water soluble film-forming polymer comprises a natural polymer selected from the group consisting of cellulose polymers, algin polymers, starch polymers, guar polymers, shellac polymers, and mixtures thereof.

14. A mascara composition according to claim 13 wherein the cellulose-based polymers are selected from the group consisting of hydroxyethylcellulose, hydroxypropylcellulose, hydroxypropyl methylcellulose, ethylhydroxyethyl cellulose and mixtures thereof.

15. A mascara composition according to claim 4 wherein the organophilic clay is organically-modified bentonite.

16. The process for making mascara compositions wherein organophilic clays are incorporated into an oil-in-water composition.

17. A mascara composition in the form of an oil-in-water emulsion, which composition is formed by a process comprising combining components comprising a water-insoluble polymeric material in an aqueous emulsion, a water-soluble film-forming polymer and an organophilic clay, wherein said clay is incorporated into the oil component of the oil-in-water emulsion.

18. The mascara composition of claim 1 wherein said water-insoluble polymeric material comprises a polymer selected from the group consisting of acrylates copolymer, styrene/acrylates/methacrylate copolymer, acrylic polymer, styrene/acrylic ester copolymer, polyvinylacetate, vinyl acetate/ethylene copolymer, styrene/butadiene copolymer, polyurethane, butadiene/acrylonitrile copolymer, styrene/acrylates/acrylonitrile copolymer, and mixtures thereof.

19. The mascara composition of claim 1 wherein said water-insoluble polymeric material comprises acrylates copolymer.

20. The mascara composition of claim 1 wherein said water-insoluble polymer material comprises styrene/acrylates/methacrylate copolymer.

21. The mascara composition of claim 1 wherein said water-insoluble polymer is a film-forming polymer.

22. The mascara composition of claim 1 wherein said water-soluble, film-forming polymer comprises a polymer formed from monomers, wherein the monomers are selected from the group consisting of vinyl alcohols.

23. The mascara composition of claim 1 wherein said water-soluble, film-forming polymer comprises vinyl alcohol/vinyl acetate copolymer.

24. The mascara composition of claim 22, further comprising a water-soluble, film-forming polymer selected from the group consisting of (i) polymers formed from monomers, wherein the monomers are selected from the group consisting of olefin oxides, vinyl pyrrolidones, vinyl esters, vinyl cyanides, oxazolines, carboxylic acids, carboxylic acid esters and mixtures thereof, (ii) polymers formed from a natural polymer, and (iii) mixtures thereof.

25. The mascara composition of claim 22, further comprising a water-solube, film-forming polymer formed from monomers, wherein the monomers are selected from the group consisting of vinyl pyrrolidones.

26. The mascara composition of claim 22, further comprising a water-soluble, film-forming polymer formed from monomers, wherein the monomers are selected from the group consisting of carboxylic acid esters.

* * * * *

UNITED STATES PATENT AND TRADEMARK OFFICE
CERTIFICATE OF CORRECTION

PATENT NO. : 6,503,495 B1  Page 1 of 1
DATED : January 7, 2003
INVENTOR(S) : Alwattari et al.

It is certified that error appears in the above-identified patent and that said Letters Patent is hereby corrected as shown below:

<u>Title page, Item [54] and Column 1, line 1,</u>
After the word "BEAUTY", insert -- BENEFITS --.

<u>Column 4,</u>
Line 20, "thereof" should read -- thereof. --.
Line 28, "/otylacrylamide" should read -- /octylacrylamide --.
Line 41, "used" should read -- useful --.

<u>Column 9,</u>
Line 54, "Ammonium Acrylates Copolymer" should read -- Ammonium Acrylates Copolymer$^4$ --.

Signed and Sealed this

Twenty-ninth Day of July, 2003

JAMES E. ROGAN
*Director of the United States Patent and Trademark Office*